(12) United States Patent
Moszner et al.

(10) Patent No.: US 6,900,251 B2
(45) Date of Patent: May 31, 2005

(54) DENTAL MATERIALS BASED ON ACRYLIC-ESTER PHOSPHONIC ACIDS

(75) Inventors: Norbert Moszner, Eschen (LT); Ulrich Salz, Lindau (DE); Frank Zeuner, Vaduz (LT); Jörg Zimmermann, Lustenau (AT); Volker Rheinberger, Vaduz (LT); Jorg Angermann, Feldkirch (AT); Urs Karl Fischer, Arbon (CH)

(73) Assignee: Ivoclar Vivadent AG, Schaan (LI)

( * ) Notice: Subject to any disclaimer, the term of this patent is extended or adjusted under 35 U.S.C. 154(b) by 126 days.

(21) Appl. No.: 10/606,142

(22) Filed: Jun. 25, 2003

(65) Prior Publication Data

US 2004/0077754 A1 Apr. 22, 2004

(30) Foreign Application Priority Data

Jun. 26, 2002 (DE) ......................................... 102 28 540
Jul. 26, 2002 (DE) ......................................... 102 34 326

(51) Int. Cl.$^7$ .............................. A61K 8/00; C07F 9/09; C08F 2/46
(52) U.S. Cl. .......................... 522/171; 522/79; 522/80; 522/84; 522/81; 522/83; 523/116; 523/117; 523/118; 568/15; 568/14
(58) Field of Search ............................. 522/81, 83, 84, 522/79, 80, 171, 175; 523/116, 117, 118; 568/15, 14, 8

(56) References Cited

U.S. PATENT DOCUMENTS

| | | | | |
|---|---|---|---|---|
| 4,537,940 A | * | 8/1985 | Omura et al. | 526/278 |
| 4,640,936 A | * | 2/1987 | Janda et al. | 522/14 |
| 4,650,847 A | * | 3/1987 | Omura et al. | 526/276 |
| 4,966,934 A | * | 10/1990 | Huang et al. | 524/315 |
| 4,968,725 A | * | 11/1990 | Mukai et al. | 522/90 |
| 5,321,053 A | * | 6/1994 | Hino et al. | 522/26 |
| 6,172,131 B1 | * | 1/2001 | Moszner et al. | 526/116 |
| 6,710,149 B2 | * | 3/2004 | Moszner et al. | 526/278 |
| 6,790,877 B2 | * | 9/2004 | Nakatsuka et al. | 523/118 |
| 2002/0143138 A1 | | 10/2002 | Moszner et al. | |

FOREIGN PATENT DOCUMENTS

| | | |
|---|---|---|
| DE | 197 46 708 C2 | 4/1999 |
| DE | 199 18 974 A1 | 12/1999 |
| DE | 100 18 968 C1 | 1/2002 |
| EP | 0 431 740 A1 * | 6/1991 |
| EP | 1 169 996 A1 | 1/2002 |
| GB | 2 089 807 A * | 6/1982 |

OTHER PUBLICATIONS

Kwamoto et al., "Novel Class of Difluorovinylphosphonate Analogues of PEP," *J. Chem. Soc. Perkin Trans.*, 1:1249–1253 (1997).

* cited by examiner

Primary Examiner—Susan Berman
(74) Attorney, Agent, or Firm—Nixon Peabody LLP

(57) ABSTRACT

Acrylic ester phosphonic acids of general formula (I), stereoisomers thereof and mixtures of these,

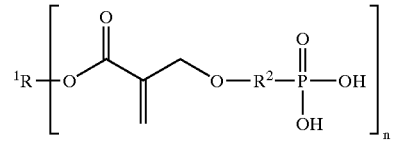

Formula I wherein n is 1 or 2, on the condition that for n=1 $R^1$ has the meaning

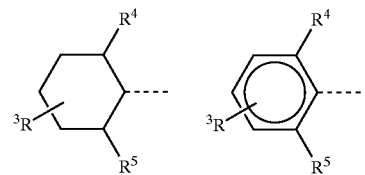

and for n=2 $R^1$ has the meaning

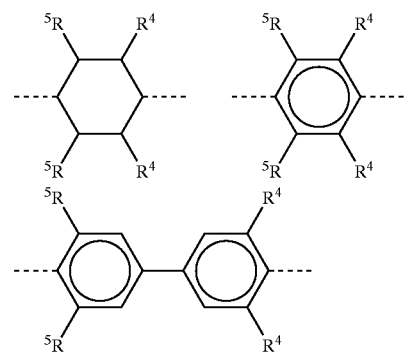

$R^2$ is a $C_1$ to $C_{12}$ alkylene radical, $C_4$–$C_8$ cycloalkylene radical or $C_7$ to $C_{15}$ alkylene phenylene radical; $R^3$ is hydrogen, a $C_1$ to $C_5$ alkyl radical or a $C_1$ to $C_5$ O-alkyl radical; and $R^4$, $R^5$, independently of each other, each stand for a $C_1$ to $C_5$ alkyl radical or a $C_1$ to $C_5$ O-alkyl radical.

19 Claims, No Drawings

DENTAL MATERIALS BASED ON ACRYLIC-ESTER PHOSPHONIC ACIDS

The present invention relates to acrylic-ester phosphonic acids which have a high hydrolysis stability and are suitable in particular for the preparation of dental materials.

Phosphonic acids capable of polymerization are of significance to polymer chemistry above all as comonomers and permit the preparation of organic polymers with high thermal stability, good adhesive properties, low flammability and good solubility in polar solvents. For this purpose, numerous monomeric phosphonic acids are synthesized and polymerized with vinyl, dienyl, allyl or styryl groups capable of polymerization. An overview of phosphonic acids is provided by Houben-Weyl, Methoden der Organischen Chemie [Methods of organic Chemistry], Volume E 20 ($2^{nd}$ part), G. Thieme Verlag, Stuttgart-New York 1987, 1300 ff. Examples of such conventional polymerizable phosphonic acids are vinyl phosphonic acid, allylbenzene phosphonic acid, α-aminoallyl phosphonic acid, 1,3-butadiene or isoprene phosphonic acid, 4-vinylbenzene phosphonic acid or 2-(4-vinylphenyl)-ethane phosphonic acid. Phosphonic acids, in which the C=C grouping is bound to the phosphorus atom directly or via an oxygen atom, such as e.g. in vinyl phosphonic acid or ethyl phosphonic acid monovinyl ester, have only a low tendency towards homopolymerization, with the result that only homopolymers with a low molar mass can be obtained.

Dental materials based on polymerizable (meth)acrylic acid derivatives of phosphonic acids, such as e.g. 2-methacryloyloxyethyl phosphonic acid, in which the (meth)acryl group capable of polymerization is bound to the phosphorus via an alkylene radical, are known from DE 199 18 974 A1. These compounds can be polymerized easily, but are not hydrolysis-stable.

DE 197 46 708 A1 discloses polymerizable acrylic phosphonic acids which are hydrolysis-stable in aqueous solution, have good adhesive properties, can be polymerized with conventional radical initiators and are therefore suitable in particular as a component of dental materials. The acrylic phosphonic acids display in the form of their carboxylic acid esters a good solubility in water and polar organic solvents while, although in the form of carboxylic acids they are easily soluble in water, they are barely soluble in organic solvents. The different solution behaviour of ester and acid can be disadvantageous in hydrous materials. The hydrolysis of the carboxylic acid ester to form free carboxylic acid accompanied by the splitting-off of alcohol can significantly change the solubility of the monomers and can thus lead to the partial or complete precipitation of the phosphonic-acid components and therefore influence the properties of the material.

DE 100 18 968 discloses dental materials based on hydrolysis-stable acrylamide and acrylonitrile phosphonic acids.

A. M. Kawamoto, M. M. Campbell, J. Chem. Soc., Perkin Trans. 1, 1997, 1249 describe difluorovinyl phosphonate analogues of phosphoenolpyruvate, which are intended to represent potential inhibitors of the shikimic acid pathway.

Finally, phosphonic-acid derivatives, in which polymerizable groups are bound via an amide group to a phosphonic acid group, such as for example in 4-methacrylamido-4-methylpentyl-phosphonic acid, are known from EP 1 169 996 A1. These compounds have only a low radical polymerization ability.

The object of the invention is to prepare acrylic phosphonic acids capable of polymerization which are characterized by a further improved resistance to hydrolysis in comparison with known acrylic phosphonic acids.

According to the invention, this object is achieved by acrylic ester phosphonic acids of general formula (I), stereoisomers thereof and mixtures of these, Formula I

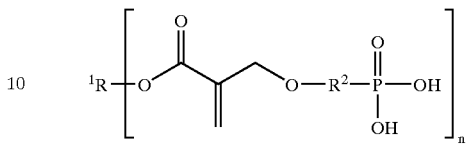

in which
n is 1 or 2,
on the condition that
for n=1 $R^1$ has the meaning

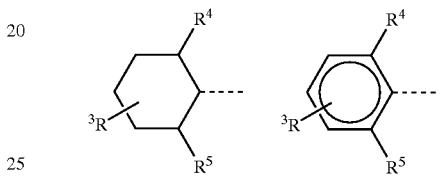

and for n=2 $R^1$ has the meaning

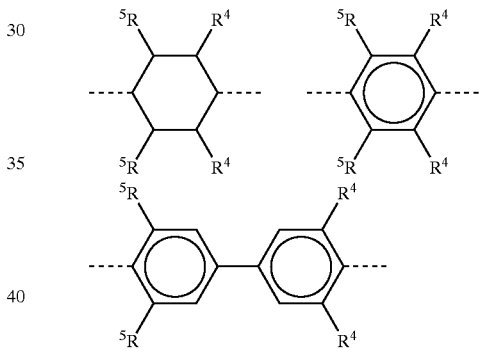

$R^2$ is a $C_1$ to $C_{12}$ alkylene radical, $C_4$–$C_8$ cycloalkylene radical or $C_7$ to $C_{15}$ alkylene phenylene radical;
$R^3$ is hydrogen, a $C_1$ to $C_5$ alkyl radical or a $C_1$ to $C_5$ O-alkyl radical; and
$R^4$, $R^5$ independently of each other, each stand for a $C_1$ to $C_5$ alkyl radical or a $C_1$ to $C_5$ O-alkyl radical.

The individual alkyl and alkylene radicals can be straight-chained, branched or cyclic.

The individual radicals R2, R3, R4 and/or R5 can be unsubstituted or substituted by one or more substituents, such as Cl, Br, $CH_3O$, OH, COOH, CN, =O, =S, =$NR^6$ or —$NR^7$—CO—C(=$CH_2$)$CH_2$—Y—$R^8$—PO(OH)$_2$, preferably Cl, $CH_3O$, OH, COOH, =O or =$NR^6$, wherein $R^6$ and $R^7$ independently of each other, each stand for hydrogen, a straight-chained or branched $C_1$ to $C_{10}$ alkyl or $C_6$ to $C_{10}$ aryl radical, preferably for hydrogen or a straight-chained $C_1$ to $C_3$ alkyl radical and $R^8$ is a straight-chained or branched $C_1$ to $C_{10}$ alkylene or $C_6$ to $C_{14}$ arylene radical, preferably a straight-chained or branched $C_1$ to $C_5$ alkylene radical or phenylene.

Furthermore, the invention relates to the use of these hydrolysis-stable acrylic ester phosphonic acids for the preparation of polymers, adhesives, dental materials or other materials and substances. The subject-matter of the present invention is also the use of the acrylic ester phosphonic acids as a component of adhesives, cements, composites, shaped bodies or dental materials as well as polymers or copolymers, which can be obtained by homo- or copolymerization of the acrylic ester phosphonic acids.

The following preferred definitions, which unless otherwise stated can be chosen independently of each other, exist for the above-mentioned variables of Formula (I):

n=1,

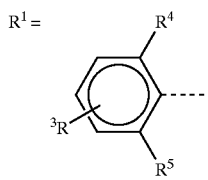

$R^2$=a $C_1$ to $C_6$ alkylene radical;
$R^3$=hydrogen, a $C_1$ to $C_3$ alkyl radical; and
$R^4$, $R^5$=independently of each other, in each case a $C_1$ to $C_3$ alkyl radical.

Preferred compounds are accordingly those in which at least one of the variables of Formula (I) has the above-described preferred definition. Particularly preferred monomers according to the invention are those in which all the variables have one of the preferred meanings.

The acrylic ester phosphonic acids of Formula (I) according to the invention can be prepared by esterification of corresponding OH-group-containing mono-(n=1) or difunctional (n=2) $R^1$—$(OH)_n$ compounds with suitable COOH-group-containing acrylate ether phosphonic acid esters AEPE analogously according to the methods for the preparation of carboxylic acid esters known from the literature (cf. among others B. Neises, W. Steglich, Angew. Chem. 90 (1978) 556, or A Hassner, V. Alexanian, Tetrahedron Lett. 46 (1978) 4475) in the presence of dicyclohexylcarbodiimide (DCC) and 4-dimethylaminopyridine (DMAP), hydrolytic splitting-off of the protective groups (SG) by silylation with trialkylsilanes, e.g. trimethylsilyl chloride/NaI or bromide (TMSBr), and subsequent reaction with alcohols, such as e.g. methanol, or water (S. Freeman, J. Chem. Soc., Perkin Trans. 2 (1991) 263.).

General:

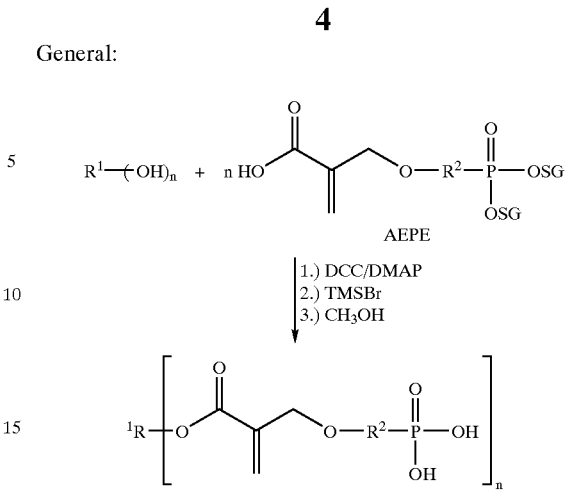

Concrete Example:

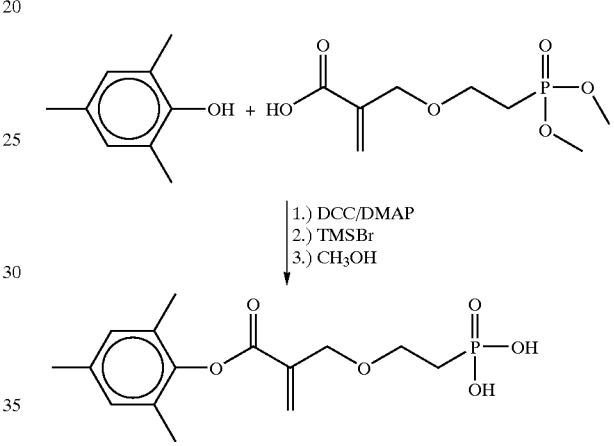

The suitable COOH-group-containing acrylate ether phosphonic acid esters AEPE can be synthesized from the corresponding carboxylic acid esters by partial hydrolysis, e.g. with an equimolar quantity of lye at −5° C. analogously to the literature (cf. N. Moszner, F. Zeuner, U. K. Fischer, V. Rheinberger, Macromol. Chem. Phys. 200 (1999) 1062).

Preferred examples of the acrylic ester phosphonic acids, according to the invention, of Formula (I) are:

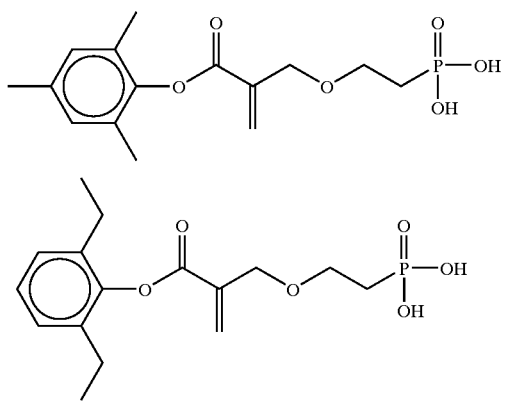

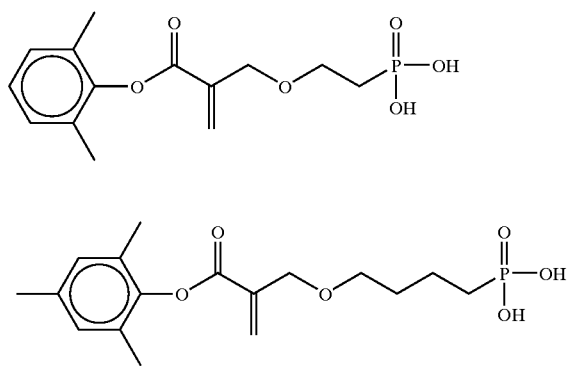

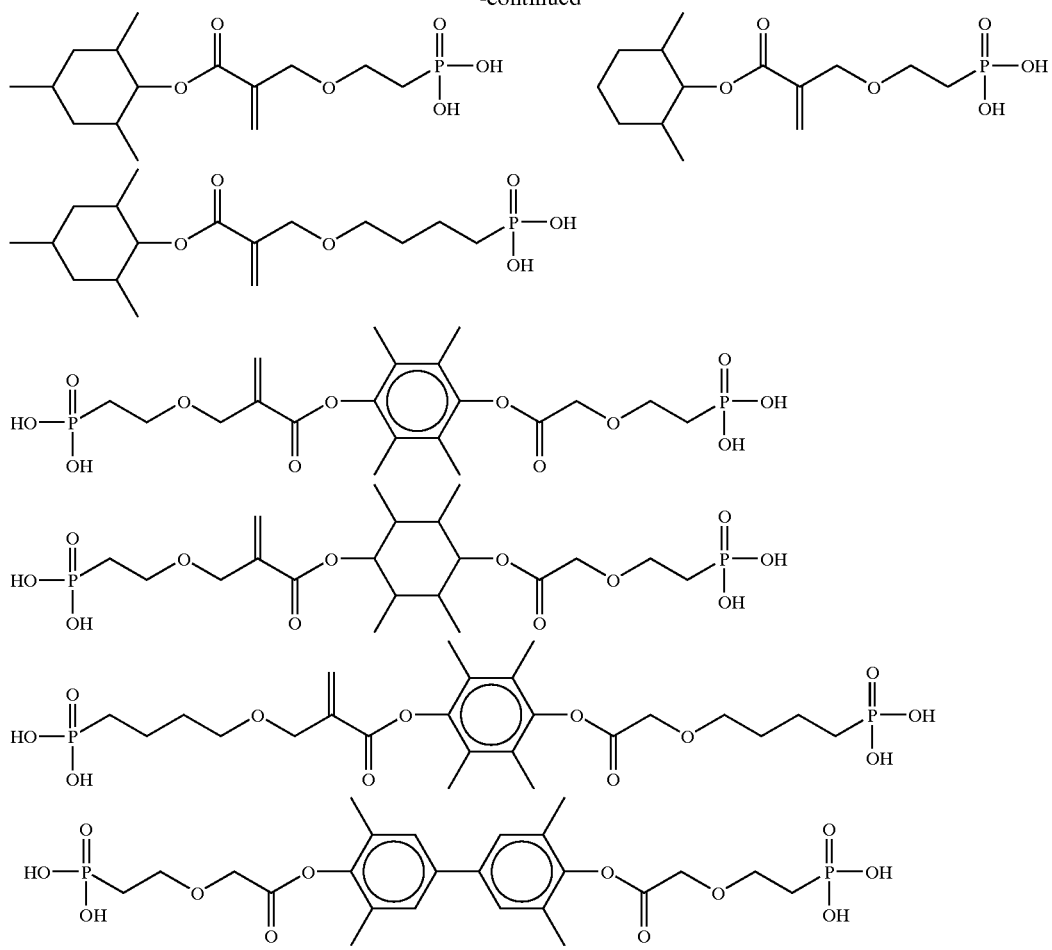

The acrylic ester phosphonic acids according to the invention are strongly acid and very easily soluble in water or mixtures of water with polar solvents, such as acetone, ethanol, acetonitrile or tetrahydrofuran (THF). In these, the acidic phosphonic-acid group is bonded to the acrylate group capable of polymerization via a hydrolysis-stable ether group. In addition, the ester group also has in the acrylic ester phosphonic acids according to the invention a high hydrolysis stability which, taken together, represents a clear improvement in comparison with conventional polymerizable acrylic phosphonic acids.

In connection with the present invention, compounds which are stable in water or in mixtures of water and water-miscible solvents in a concentration of approx. 20 wt.-% and a pH value of approx. 2.0 at 37° C. for at least 6 weeks, i.e. hydrolyze to less than 1%, are described as hydrolysis-stable.

As a result of the presence of polymerizable groups, the acrylic phosphonic acid esters according to the invention are suitable as starting materials for the preparation of polymers and copolymers. They can be homopolymerized with the known methods of radical polymerization or copolymerized e.g. with suitable comonomers.

The acrylic ester phosphonic acids according to the invention can be used in free form or in the form of their salts, i.e. as phosphonates or phosphonate esters, wherein, in the case of the salts, preferably alkali metal ions, in particular sodium and lithium ions, as well as organic ammonium ions serve as counterions, in particular those which are derived from amine accelerators, such as N,N-dihydroxyethyl-p-toluidine, N,N-bis(2-hydroxy-3-methacryloxypropyl-3,5-xylidine or 4-(dimethylamino)-benzoic acid-2-ethyl-hexylester. Amine accelerators are used in dentistry as a component for example of photoinitiator systems. Generally tert.amines are involved which can act as H-donors and therefore accelerate radical formation (cf. L. A. Linden, "Photocuring of Polymeric Dental Materials and Plastic Composite Resins" in Radiation Curing in Polymer Science and Technology, Vol. IV, J. P. Fouassier, J. F. Rabek (Ed.), Elsevier Appl. Sci., London, New York 1993, 396f.).

The known radical initiators can be used to carry out polymerization (cf. Encyclopedia of Polymer Science and Engineering, Vol. 13, Wiley-Interscience Publisher, New York 1988, 754 ff.).

In order to initiate radical photopolymerization, preferably benzophenone, benzoin as well as their derivatives or α-diketones or their derivatives such as 9,10-phenanthrenequinone, 1-phenyl-propane-1,2-dion, diacetyl or 4,4-dichlorobenzyl can be used. Preferably camphorquinone and 2,2-methoxy-2-phenyl-acetophenone and particularly preferably α-diketones are used in combination with amines as reducing agents, such as e.g. 4-(dimethylamino)-benzoic-acid ester, N,N-dimethylaminoethyl methacrylate, N,N-dimethyl-sym.-xylidine or triethanolamine.

In particular azo compounds, such as azobis (isobutyronitrile) (AIBN) or azobis-(4-cyanovaleric acid) or peroxides, such as dibenzoyl peroxide, dilauroyl peroxide, tert.-butyl peroctoate, tert.-butyl perbenzoate or di-(tert.-butyl)-peroxide are suitable as thermal initiators. Benzopinacol and 2,2'-dialkyl benzopinacols are also suitable as initiators for hot-curing. Redox initiator combinations, such as e.g. combinations of benzoyl peroxide with N,N-dimethyl-sym.-xylidine or N,N-dimethyl-p-toluidine, are used as initiators for a polymerization carried out at room temperature. In addition, redox systems consisting of peroxides and such reducing agents, such as e.g. ascorbic acid, barbiturates or sulphinic acids, are also particularly suitable.

The subject-matter of the invention is also compositions which contain one or more acrylic ester phosphonic acids according to Formula (I) and additionally also an initiator for radical polymerization.

As a result of the hydrolysis stability of the acrylic ester phosphonic acids according to the invention, the compositions are storage-stable at room temperature even in the presence of water and are suitable in particular as adhesives or cements above all for dental applications.

Compositions are also preferred which, in addition to acrylic ester phosphonic acid and optionally initiators, also contain one or more radically polymerizable monomers.

Monofunctional and/or multifunctional radically polymerizable monomers, in particular difunctional crosslinking monomers, are suitable as comonomers. By monofunctional monomers is meant compounds with one radically polymerizable group, by multifunctional monomers is meant compounds with two and more radically polymerizable groups. Above all crosslinking bi- or multifunctional acrylates or methacrylates, such as e.g. bisphenol-A-di(meth)acrylate, bis-GMA (the addition product of methacrylic acid and bisphenol-A-diglycidyl ether), UDMA (the addition product of hydroxyethyl methacrylate and 2,2,4-trimethylhexamethylene diisocyanate), di-, tri- or tetraethylene glycol di(meth)acrylate, trimethylolpropane tri(meth) acrylate and pentaerythrite tetra(meth)acrylate, are suitable for the preparation of adhesives or dental materials. The compounds butanediol di(meth)acrylate, 1,10-decanediol di(meth)acrylate and 1,12-dodecanediol di(meth)acrylate, which can be obtained by esterification of (meth)acrylic acid with the corresponding diols, are also suitable.

Particularly preferred radically polymerizable monomers are acrylamides or hydroxyalkyl acrylamides.

As a result of their hydrolysis stability, amides of general formula $BX_n$ are particularly preferred, in which
B stands for a hydrocarbon radical with 1 to 50 carbon atoms, substituted n times by the group X', which can contain one or more of the groups O, S, NH, CO—NH, NH—CO, NH—CO—O, O—CO—NH and/or NH—CO—NH,
X' stands for the group

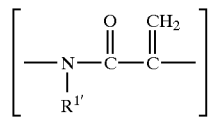

which is bound to the radical B via the nitrogen atom or via C-2, the binding site not connected to B carrying a radical $R^{2'}$.
$R^{1'}$ is hydrogen, an alkyl group with 1 to 20 carbon atoms or a phenyl radical, wherein two or more radicals X' can share a radical $R^{1'}$ and wherein $R^{1'}$ can also be a component of the radical B,
$R^{2'}$ is hydrogen, an alkyl group with 1 to 20 carbon atoms or a phenyl radical, and n' is a number from 2 to 5.

Group X' represents the N-substituted amide groups which are bound to the radical B via amide nitrogen or via the carbon atom C-2.

Amides of this type, preferred derivatives thereof and their preparation are disclosed in DE 101 01 523.

Also preferred are hydroxyalkyl acrylamides of the formula

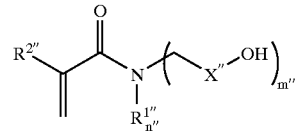

in which
X" stands for a $C_1$ to $C_{12}$ alkylene radical or $C_7$ to $C_{15}$ alkylene phenylene radical, preferably for a $C_1$ to $C_{10}$ alkylene radical and quite particularly preferably for a $C_1$ to $C_8$ alkylene radical,
—$R^{1"}$ stands for a $C_1$ to $C_{10}$ alkyl radical, phenyl or hydrogen, preferably for a $C_1$ to $C_6$ alkyl radical or hydrogen, particularly preferably a $C_1$ to $C_3$ alkyl radical or hydrogen,
m",n" independently of each other, are 0, 1 or 2, where m"+n" is equal to 2, and
$R^{2"}$ stands for hydrogen, methyl or X'"—OH, if m" is greater than or equal to 1, or for X'"—OH, if m" is equal to 0, where X'" has one of the meanings given for X" and is preferably a $C_1$ to $C_6$ alkylene, particularly preferably a $C_1$ to $C_3$ alkylene, and
where for n"=2 the two radicals $R^{1"}$ and for m"=2 the two radicals —X"— can be the same or different. The above hydroxyalkyl acrylamides contain no aldehyde groups.

The named alkyl and alkylene radicals are preferably linear groups. Compounds in which m" und n" are each equal to 1 are particularly preferred. Compounds which have 1, 2 or 3 hydroxyl groups per molecule are also preferred.

Hydroxyalkylamides of this type, preferred derivatives thereof and their preparation are described in DE 102 28 540.

Preferred monofunctional radically polymerizable monomers which are suitable in particular as diluting monomers are hydrolysis-stable mono(meth)acrylates, such as e.g. mesityl methacrylate, or 2-(alkoxymethyl)acrylic acids, such as e.g. 2-(ethoxymethyl)acrylic acid, 2-(hydroxymethyl)acrylic acid, N-mono- or -disubstituted acrylamides, such as e.g. N-ethylacrylamide, N,N-dimethacrylamide, N-(2-hydroxyethyl)acrylamide or N-(2-hydroxyethyl)-N-methyl-acrylamide, as well as N-monosubstituted methacrylamides, such as e.g. N-ethylmethacrylamide or N-(2-hydroxyethyl) methacrylamide and also N-vinylpyrrolidone or allyl ether.

Preferred multifunctional radically polymerizable monomers which are suitable in particular as crosslinking monomers are hydrolysis-stable urethanes from 2-(hydroxymethyl)acrylic acid and diisocyanates, such as e.g. 2,2,4-trimethyl hexamethylene diisocyanate or isophorone diisocyanate, crosslinking pyrrolidones, such as e.g. 1,6-bis(3-vinyl-2-pyrrolidonyl)hexane, or commercially available bisacrylamides such as methylene or ethylene bisacrylamide, or bis(meth)acrylamides, such as e.g. N,N'-diethyl-1,3-bis(acrylamido)-propane, 1,3-bis(methacrylamido)-propane, 1,4-bis(acrylamido)-butane or 1,4-bis(acryloyl)-piperazine, which can be synthesized by reaction from the corresponding diamines with (meth) acrylic acid chloride.

The compositions can contain one or more of the named comonomers. Compositions which contain at least one multifunctional radically polymerizable monomer are preferred.

Furthermore, the compositions according to the invention for improving the mechanical properties or for setting the viscosity can be filled with organic or inorganic particles. Preferred inorganic particulate fillers are amorphous spherical materials based on oxides, such as $ZrO_2$ and $TiO_2$ or mixed oxides of $SiO_2$, $ZrO_2$ and/or $TiO_2$, nanoparticulate or microfine fillers, such as pyrogenic silicic acid or precipitation silicic acid as well as mini fillers, such as quartz, glass ceramic or glass powder with an average particle size of 0.01 to 1 µm as well as x-ray opaque fillers, such as ytterbium trifluoride or nanoparticulate tantalum(V) oxide or barium sulphate.

Furthermore, the compositions according to the invention can contain radically polymerizable phosphoric-acid derivatives. Hydrolysis-stable phosphoric-acid derivatives, such as (meth)acrylamidoalkyl dihydrogen phosphates, in particular 6-(N-methacryloylamino)hexyl- and 2-(N-methacryloylamino)ethyl-dihydrogen phosphate, are preferred. These compounds improve the etching effect of the composition and are therefore suitable in particular for the preparation of self-etching dental materials, such as adhesives and cements. Here, alkyl stands for $C_1$ to $C_{12}$ alkyl, preferably for $C_1$ to $C_6$ alkyl.

In addition, the compositions according to the invention also contain preferably a solvent, such as ester, e.g. ethyl acetate, preferably water, ethanol, acetone, methylene chloride, acetonitrile or mixtures thereof. Compositions which contain water or a hydrous solvent mixture as solvent are preferred.

The compositions according to the invention can also contain further additives, e.g. stabilizers, aromatics, microbiocidal active ingredients, fluoride-ion-releasing additives, optical brighteners, plasticizers and/or UV absorbers.

Compositions which contain exclusively hydrolysis-stable components corresponding to the above definition, represent a quite particularly preferred version of the invention.

The compositions according to the invention are suitable in particular for the preparation of dental materials, such as cements, for example of self-adhesive fixing cements, and in particular of adhesives. Such adhesives are characterized by a very good adhesion to the tooth hard substance and are hydrolysis-stable under moist conditions.

Preferred dental materials contain the following components (a), (b), (c), (d), (e) and/or (f):

a) 0.5 to 70 wt.-%, preferably 10 to 60 wt.-% and particularly preferably 15 to 50 wt.-% acrylic ester phosphonic acid according to Formula (I), b) 0.01 to 15 wt.-%, particularly preferably 0.1 to 8.0 wt.-% initiator for radical polymerization, c) 0 to 80 wt.-%, preferably 0 to 60 wt.-% and particularly preferably 10 to 50 wt.-% radically polymerizable monomer, d) 0 to 95 wt.-%, preferably 0 to 80 wt.-%, particularly preferably 10 to 70 wt.-% and quite particularly preferably 20 to 60 wt.-% solvent, e) 0 to 50 wt.-%, preferably 0 to 30 wt.-%, particularly preferably 0 to 20 wt.-% and quite particularly preferably 10 to 20 wt.-% (meth)acrylamidoalkyl dihydrogen phosphate, f) 0 to 75 wt.-%, particularly preferably—depending on the use—0 to 20 wt.-% (adhesive) or 20 to 75 wt.-% (cement) filler.

Compositions which contain at least the components (a), (c) and (d) are particularly preferred.

The invention is explained in detail in the following with reference to examples.

EXAMPLES

Example 1

Synthesis of 2-[2-dihydroxyphosphoryl)-ethoxymethyl]-acrylic acid-2,4,6-trimethyl-phenyl ester (MAPA)

Stage 1: 2-[2-dimethoxyphosphoryl)-ethoxymethyl]-acrylic acid-2,4,6-trimethyl-phenyl ester (MAPAME)

24.5 g (128 mmol) N-(3-dimethylaminopropyl)-N'-ethylcarbodiimide-hydrochloride was added in portions within 3 h under vigorous stirring to a solution of 27.6 g (116 mmol) 2-[4-(dimethoxyphosphoryl)-2-oxabutyl]-acrylic acid, which was prepared according to the literature (N. Moszner, F. Zeuner, S. Pfeiffer, I. Schurte, V. Rheinberger, M. Drache, Macromol. Mater. Eng. 286 (2001) 225) by partial hydrolysis of 2-[4-(dimethoxyphosphoryl)-2-oxabutyl]-acrylic acid ethyl ester, 1.33 g (11 mmol) 4-dimethylaminopyridine and 15.0 g (116 mmol) mesitol in 60 ml THF. The mixture was left to react further overnight at room temperature. The volatile components were then drawn off and the remaining oily residue was taken up in 250 ml methylene chloride. The mixture was extracted with 0.5N hydrochloric acid, washed neutral and dried over anhydrous sodium sulphate. Finally, all the volatile components were separated in fine vacuum and the crude product purified by means of column chromatography: silica gel column, mobile solvent THF/toluene 1:1. 11.9 g MAPAME (29% yield) as colourless oil is obtained.

$^1$H-NMR (400 MHz, $CDCl_3$, ppm): 2.10 (s, 6H, o-$CH_3$), 2.17 (dt, 2H, $PCH_2$), 2.27 (s, 3H, p-$CH_3$), 3.75 (d, 6H, =$CH_3$), 3.81 (m, 2H, $PCH_2C\underline{H}_2$), 4.34s, 2H, $OCH_2C$=), 6.07 and 6.56 (2s, 1H, =$CH_2$), and 6.87 (s, 2H, $C_{ar}H$).

$^{13}$C-NMR ($CDCl_3$, 100 MHz): 16.1 ($OC_{ar.}\ C_{ar.}\underline{C}H_3$), 20.8 ($OC_{ar.}\ C_{ar.}\ C_{ar.}\ C_{ar.}\underline{C}H_3$), 24.8 (d, $P\underline{C}H_2CH_2$, $^1J_{C,P}$=140.2 Hz), 52.3 (d, $OCH_3$, $^2J_{C,P}$=6.5 Hz), 64.7 ($PCH_2\underline{C}H_2$), 69.2 ($O\underline{C}H_2C$=), 127.4 (C=$\underline{C}H_2$), 129.2 ($C_{ar.}H$), 129.7 ($OC_{ar.}\ \underline{C}_{ar.}CH_3$), 135.4 ($OC_{ar.}\ C_{ar.}\ C_{ar.}\ \underline{C}_{ar.}\ CH_3$), 136.4 ($\underline{C}$=$CH_2$), 145.7 ($OC_{ar.}$), 163.7 (C=O).

$^{31}$P-NMR ($CDCl_3$, 162 MHz): δ=+32.5.

Stage 2: 2-[2-dihydroxyphosphoryl)-ethoxymethyl]-acrylic acid-2,4,6-trimethyl-phenyl ester 10.56 g (69 mmol) trimethylsilyl bromide was carefully added dropwise under argon to a mixture of 9.83 g (27.6 mmol) of the compound MAPAME and 2.7 mg phenothiazine MEHQ and stirred for 3 h at 45° C. Then the mixture was evaporated in a rotary evaporator, reacted with 60 ml methanol, stirred overnight, evaporated in fine vacuum and dried to constant weight. 8.77 g (97% yield) of a very viscous oil of MAPA remained.

$^1$H-NMR ($CDCl_3$, 400 MHz): δ=2.08 (s, 6H, o-$CH_3$), 2.18 (dt, 2H, $PCH_2$), 2.26 (s, 3H, p-$CH_3$), 3.82 (m, 2H, $PCH_2C\underline{H}_2$), 4.31 (s, 2H, $OCH_2C$=), 6.06, 6.55 (in each case s, 1H, =$CH_2$), 6.86 (s, 2H, $C_{ar.}H$), 9.48 (br, 2H, POH).

$^{13}$C-NMR ($CDCl_3$, 100 MHz): δ=16.2 ($OC_{ar.}\ C_{ar.}\ \underline{C}H_3$), 20.8 ($OC_{ar.}\ C_{ar.}\ C_{ar.}\ C_{ar.}\ \underline{C}H_3$), 26.8 (d, $P\underline{C}H_2CH_2$, $^1J_{C,P}$=143.6 Hz), 64.6 ($PCH_2\underline{C}H_2$), 69.2 ($O\underline{C}H_2C$=), 127.9 ($\underline{C}$=$CH_2$), 129.2 ($C_{ar.}H$), 129.7 ($OC_{ar.}\ \underline{C}_{ar.}\ CH_3$), 135.4 ($OC_{ar.}\ C_{ar.}\ C_{ar.}\ \underline{C}_{ar.}\ CH_3$), 136.1 ($\underline{C}$=$CH_2$), 145.7 ($OC_{ar.}$), 163.8 (C=O).

$^{31}$P-NMR ($CDCl_3$, 162 MHz): δ=+33.6.

Example 2

Examination of the Hydrolysis Stability of MAPA

A 20% solution of MAPA, stabilized with 200 ppm 2,6-di-t-butyl-4-methylphenol, was prepared in $D_2O/EtOH$-$d_6$ (1:1), stored at 37° C. and $^1$H-NMR-spectroscopically examined. After a standing time of 2 months, no changes in the $^1$H-NMR-spectrum were able to be detected.

Example 3

Preparation of Chemically Curing Adhesives Based on MAPA

In order to examine dentine adhesion to bovine-tooth dentine, adhesives with the following composition were prepared (figures in wt.-%):

TABLE 1

Composition and coefficients of adhesion for dental adhesives based on MAPA

| MAPA | Comonomer | Water | Initiator | Coefficients of adhesion |
|---|---|---|---|---|
| 16% | 17% HMA [1] | 60% | 7% | 9.1 ± 2.1 MPa |
| 16% | 17% MAHP [2] | 60% | 7% | 11.0 ± 3.5 MPa |
| 20% | 13% HEMAM [3] | 60% | 7% | 11.0 ± 2.0 MPa |
| 16% | 17% DEPBAM [4] | 60% | 7% | 8.8 ± 2.4 MPa |

[1] HMA = 2-(hydroxymethyl)acrylic acid
[2] MAHP = 6-(N-methacryloylamino)hexyl-dihydrogen phosphate
[3] HEMAM = N-(2-hydroxyethyl)-N-methyl-acrylamide
[4] DEPBAM = N,N'-diethyl-1,3-propylene-bisacrylamide Bovine teeth were embedded into plastic cylinders such that the dentine and the plastic were located at one level. One layer each of the above adhesives was massaged for 15 s into the dentine surface with a small brush and lightly blown with an air syringe. A prepolymerized cylinder, made from dental composite material (Tetric® Ceram, Ivoclar Vivadent AG), coated with a self-curing cement was applied to the adhesive layer and cured for 10 minutes in the dark. The test pieces were then stored in water for 24 h at 37° C. and the shearing adhesive strength was determined according to the ISO Guideline "ISO 1994-ISO TR 11405: Dental Materials Guidance on Testing of Adhesion to Tooth Structure". The results are summarized in Table 1. They show that the acrylic ester phosphonic acids according to the invention are not only hydrolysis-stable, but also guarantee a high degree of adhesion between dentine and composite material.

What is claimed is:

1. Acrylic ester phosphonic acid of formula (I), stereoisomers thereof and mixtures of these,

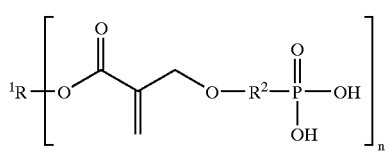

Formula I in which
n is 1 or 2,
on the condition that
for n=1 $R^1$ has the meaning

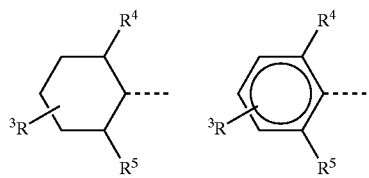

and for n=2 $R^1$ has the meaning

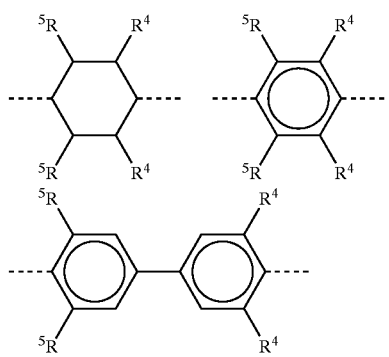

$R^2$ is a $C_1$ to $C_{12}$ alkylene radical, $C_4$–$C_8$ cycloalkylene radical or $C_7$ to $C_{15}$ alkylene phenylene radical;
$R^3$ is hydrogen, a $C_1$ to $C_5$ alkyl radical or a $C_1$ to $C_5$ O-alkyl radical; and
$R^4$, $R^5$ independently of each other, each stand for a $C_1$ to $C_5$ alkyl radical or a $C_1$ to $C_5$ O-alkyl radical.

2. Acrylic ester phosphonic acid according to claim 1, wherein one or more of the variables of Formula (I), independently of each other, have the following meaning:
n=1, $R^1 =$ 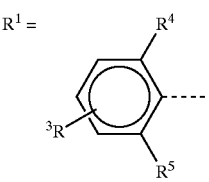

$R^2$=a $C_1$ to $C_6$ alkylene radical;
$R^3$=hydrogen, a $C_1$ to $C_3$ alkyl radical; and
$R^4$, $R^5$=independently of each other, a $C_1$ to $C_3$ alkyl radical.

3. Acrylic ester phosphonic acid according to claim 1 wherein the radicals $R^2$, $R^3$, $R^4$ and/or $R^5$ are unsubstituted or substituted by one or more substituents selected from the group Cl, Br, $CH_3O$, OH, COOH, CN, =O, =S, =$NR^6$ or —$NR^7$—CO—C(=$CH_2$)$CH_2$—Y—$R^8$—PO(OH)$_2$, wherein $R^6$ and $R^7$, independently of each other, each stand for hydrogen, a straight-chained or branched $C_1$ to $C_{10}$ alkyl or $C_6$ to $C_{10}$ aryl radical and $R^8$ is a straight-chained or branched $C_1$ to $C_{10}$ alkylene or $C_6$ to $C_{14}$ arylene radical.

4. Composition containing an acrylic ester phosphonic acid according to claim 1.

5. Composition according to claim 4, further comprising a radically polymerizable monomer.

6. Composition according to claim 5, containing an acrylamide and/or a hydroxyalkyl acrylamide as a radically polymerizable monomer.

7. Composition according to claim 5, containing a monofunctional and/or a multifunctional radically polymerizable monomer.

8. Composition according to claim 7, containing as a monofunctional radically polymerizable monomer one or more hydrolysis-stable mono(meth)acrylates, mesityl methacrylate, one or more 2-(alkoxymethyl)acrylic acids, 2-(ethoxymethyl)acrylic acid, 2-(hydroxymethyl)acrylic acid, one or more N-mono- or N-disubstituted acrylamides, N-ethylacrylamide, N,N-dimethacrylamide, N-(2-hydroxyethyl)acrylamide, N-(2-hydroxyethyl)-N-methyl-acrylamide, one or more N-monosubstituted methacrylamides, N-ethymethacrylamide, N-(2-hydroxyethyl)methacrylamide, N-vinylpyrrolidone, allyl ether or a mixture of two or more of these monomers.

9. Composition according to claim 7, containing as a multifunctional radically polymerizable monomer one or more urethanes from 2-(hydroxymethyl)acrylic acid and diisocyanates, 2,2,4-trimethylhexamethylene diisocyanate, isophorone diisocyanate, one or more crosslinking pyrrolidones, 1,6-bis(3-vinyl-2-pyrrolidonyl)-hexane, one or more bisacrylamides, methylene bisacrylamide, ethylene bisacrylamide, one or more bis(meth)acrylamides, N,N'-diethyl-1,3-bis(acrylamido)-propane, 1,3-bis(methacrylamido)-propane, 1,4-bis(acrylamido)-butane, 1,4-bis(acryloyl)-piperazine or a mixture of two or more of these monomers.

10. Composition according to claim 9, further comprising an initiator for radical polymerization.

11. Composition according to claim 4, further containing a filler.

12. Composition according to claim 4, further comprising a solvent.

13. Composition according to claim 4, further comprising a (meth)acrylamidoalkyl dihydrogen phosphate.

14. Composition according to claim 4, containing
   a) 0.5 to 70 wt.-% of the acrylic ester phosphonic acid;
   b) 0.01 to 15 wt.-% initiator for radical polymerization;
   c) 0 to 80 wt.-% radically polymerizable monomer;
   d) 0 to 95 wt.-% solvent;
   e) 0 to 50 wt.-%, (meth)acrylamidoalkyl dihydrogen phosphate, and/or
   f) 0 to 75 wt.-% of filler.

15. A dental material comprising a composition according to claim 4.

16. A cement or adhesive comprising a composition according to claim 4.

17. A dental material comprising an acrylic ester phosphonic acid according to claim 1.

18. Composition containing an acrylic ester phosphonic acid according to claim 2.

19. Composition according to claim 18, containing
   a) 0.5 to 70 wt.-% of the acrylic ester phosphonic acid;
   b) 0.01 to 15 wt.-% initiator for radical polymerization;
   c) 0 to 80 wt.-% radically polymerizable monomer;
   d) 0 to 95 wt.-% solvent;
   e) 0 to 50 wt.-%, (meth)acrylamidoalkyl dihydrogen phosphate, and/or
   f) 0 to 75 wt.-% filler.

* * * * *